(12) United States Patent
Snow

(10) Patent No.: US 8,241,254 B2
(45) Date of Patent: Aug. 14, 2012

(54) MEDICAL NEEDLE SYSTEMS WITH RESET DEVICES FOR MEDICAL NEEDLE SHIELD APPARATUS

(75) Inventor: Jeremy W. Snow, Salt Lake City, UT (US)

(73) Assignee: Specialized Health Products, Inc., Salt Lake City, UT (US)

( * ) Notice: Subject to any disclaimer, the term of this patent is extended or adjusted under 35 U.S.C. 154(b) by 867 days.

(21) Appl. No.: 11/918,330

(22) PCT Filed: Apr. 13, 2006

(86) PCT No.: PCT/US2006/014260
§ 371 (c)(1),
(2), (4) Date: Oct. 11, 2007

(87) PCT Pub. No.: WO2006/113542
PCT Pub. Date: Oct. 26, 2006

(65) Prior Publication Data
US 2009/0043262 A1   Feb. 12, 2009

(51) Int. Cl.
*A61M 5/32* (2006.01)
(52) U.S. Cl. .................................. 604/198; 604/192
(58) Field of Classification Search .............. 604/110, 604/164.08, 192, 197, 198, 263, 111
See application file for complete search history.

(56) References Cited

U.S. PATENT DOCUMENTS

| | | | |
|---|---|---|---|
| 4,425,120 A | 1/1984 | Sampson et al. | |
| 4,666,435 A | 5/1987 | Braginetz | |
| 5,595,566 A | 1/1997 | Vallelunga et al. | |
| 6,063,037 A * | 5/2000 | Mittermeier et al. | 600/567 |
| 6,254,575 B1 | 7/2001 | Thorne, Jr. et al. | |
| 7,179,244 B2 | 2/2007 | Smith et al. | |
| 2002/0133122 A1 | 9/2002 | Giambattista et al. | |
| 2003/0100868 A1 | 5/2003 | Ferguson et al. | |
| 2003/0120209 A1* | 6/2003 | Jensen et al. | 604/110 |
| 2005/0277893 A1* | 12/2005 | Liversidge | 604/198 |

FOREIGN PATENT DOCUMENTS
WO   WO-2005053774 A1   6/2005

OTHER PUBLICATIONS

Jul. 6, 2006 International Search Report in international application No. PCT/US06/14260.
Jul. 6, 2006 Written Opinion of the ISA in international application No. PCT/US06/14260.
Apr. 30, 2007 International Preliminary Report on Patentability in international application No. PCT/US06/14260.
Apr. 7, 2005 International Search Report in international application No. PCT/U504/39400.
Apr. 7, 2005 Written Opinion of the ISA in international application No. PCT/US04/39400.
Jul. 25, 2005 International Preliminary Report on Patentability in international application No. PCT/US04/39400.

* cited by examiner

*Primary Examiner* — Kevin C. Sirmons
*Assistant Examiner* — Kami A Bosworth
(74) *Attorney, Agent, or Firm* — Rutun & Tucker, LLP

(57) ABSTRACT

A medical needle shield system is provided that includes a medical needle shield apparatus and a reset device. The reset device resets a safety housing on the medical needle. The reset device has alignment features which guide the safety housing towards reset features. The reset features pass through access features in the safety housing to reset the reset geometry so that the safety housing no longer sheathes a tip of the medical needle.

20 Claims, 6 Drawing Sheets

MEDICAL NEEDLE SYSTEMS WITH RESET DEVICES FOR MEDICAL NEEDLE SHIELD APPARATUS

TECHNICAL FIELD

The present invention relates generally to safety shields for medical needles, and more particularly, to safety shields that protect a needle point of a medical needle.

DESCRIPTION OF THE RELATED ART

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogen exposures.

Procedures for removing a needle from a patient commonly require a technician to use one hand to place pressure at the wound site where the needle is being withdrawn, while removing the needle device with the other hand. It is also common practice for an attending technician to give higher priority to care for the patient than is given to disposal of a needle. In the case of typical needle devices without safety shields, such priority either requires the convenience of an available sharps container within reach or another means for safe disposal without leaving the patient's side. Providing adequate care while following safety procedures is often compounded by the patient's physical condition and mental state, such as in burn units and psychiatric wards. Under such conditions, it is difficult to properly dispose of a used needle while caring for a patient.

The widespread knowledge and history associated with needle care and disposal problems have resulted in numerous devices for preventing accidental needle sticks. Problems of current safety devices include difficulty of use and high cost due to their complexity and number of parts.

Other known devices employ sheaths that are spring activated, telescoping, pivoting, etc. These devices, however, may disadvantageously misfire or be cumbersome to activate. Further drawbacks of current devices include high manufacturing cost due to complexity and the number of parts. Thus, these type prior art devices may not adequately and reliably shield medical needle apparatus to prevent hazardous exposure.

Consequently, there remains a need to provide a more satisfactory solution for needle safety devices by overcoming the disadvantages and drawbacks of the prior art. Therefore, it would be desirable to provide a more adequate and reliable medical needle shield apparatus that employs a safety shield slidably movable along a medical needle to prevent hazardous exposure to a needle tip. It would be advantageous to provide such a safety shield that is capable of being reset to safely allow re-use of certain needle apparatus. Such a needle shield apparatus should be easily and reliably movable to shield a needle tip of a needle cannula.

BRIEF DESCRIPTION OF THE DRAWINGS

Understanding that drawings depict only typical embodiments of the invention and are not therefore to be considered to be limiting of its scope, the invention will be described and explained with additional specificity and detail through the use of the accompanying drawings as listed below.

DETAILED DESCRIPTION OF THE EXEMPLARY EMBODIMENTS

Figure 1:
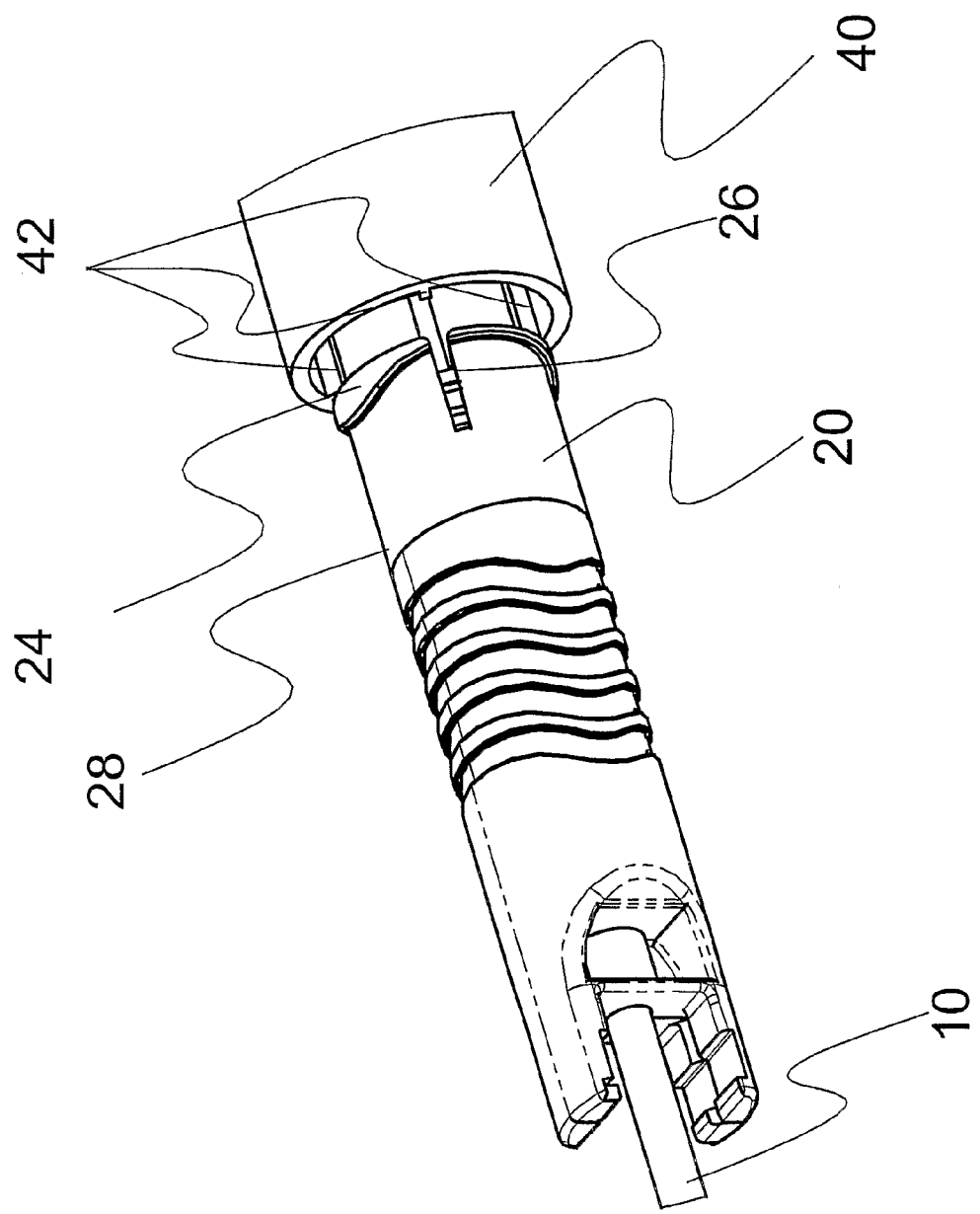
FIG. 1 is a perspective view of an embodiment of a safety housing and an embodiment of an obturator handle.

The exemplary embodiments of the medical needle shield apparatus and methods of operation disclosed are discussed in terms of medical needles for infusion of intravenous fluids, medication infusion or fluid collection, guiding of other needles, e.g., biopsy, and more particularly, in terms of needle shield apparatus employed with a needle cannula that prevent hazardous exposure to the needle tip, including, for example, inadvertent needle sticks. It is envisioned that the present disclosure, however, finds application to a wide variety of cannula needles and devices for the infusion of preventive medications, medicaments, therapeutics, etc. to a subject, such as, for example, epidural needles, spinal needles, biopsy needles, chiba needles, potts coumand needles, coaxial introducer needles, Y-sites, etc. It is also envisioned that the present disclosure may be employed for collection of body fluids and/or tissues, including those employed during procedures relating to soft tissue biopsy, bone biopsy, phlebotomy, digestive, intestinal, urinary, veterinary, etc. It is contemplated that the medical needle shield apparatus may be utilized with other medical needle applications including, but not limited to, fluid infusion, fluid collection, catheters, catheter introducers, guidewire introducers, biopsy needle introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the medical needle shield apparatus. According to the present disclosure, the term "clinician" refers to an individual administering an infusion, performing fluid or tissue collection, installing or removing a needle cannula from a medical needle shield apparatus and may include support personnel.

The following discussion includes a description of the medical needle shield apparatus, followed by a description of the method of operating the medical needle shield apparatus in accordance with the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1-5, there is illustrated a medical needle system comprising a medical needle shield apparatus and a reset device, which are constructed in accordance with the principles of the present disclosure.

FIGS. 1-5 depict the sequential use of an embodiment which enables a locked safety housing to be reset for use again in a medical procedure by being mated with a reset device. This is useful, for example, when a medical needle shield apparatus is used in a medical procedure for a subject and it is necessary to re-use the apparatus again on the subject. The reset device may also have at least one other functionality in the medical procedure. Examples of other uses in the medical procedure are provided below. Of course, the reset device may have the sole purpose of unlocking the safety housing.

FIG. 1 depicts a medical needle 10 and the distal end of a safety housing 20 which is part of a medical needle shield apparatus. The distal end of needle 10 is not visible in FIG. 1 because the needle has been used in a medical procedure and safety housing 20 has been locked onto needle 10 via a binding member such as a clip which is not shown. Numerous examples of binding members are disclosed in U.S. patent application Ser. No. 10/721,526 titled Resettable Safety Shield for Medical Needles which was filed on Nov. 25, 2003 and was published as U.S. Patent Publication No. 2004/0078003. Numerous examples of binding members are also disclosed in International Patent Application No. PCT/US2004/039400 which was filed on Nov. 23, 2004 and was published as International Publication No. WO 2005/053774 on Jun. 16, 2005. U.S. Patent Publication No. 2004/0078003 and International Publication No. WO 2005/053774 are both hereby incorporated by reference.

Figure 3:
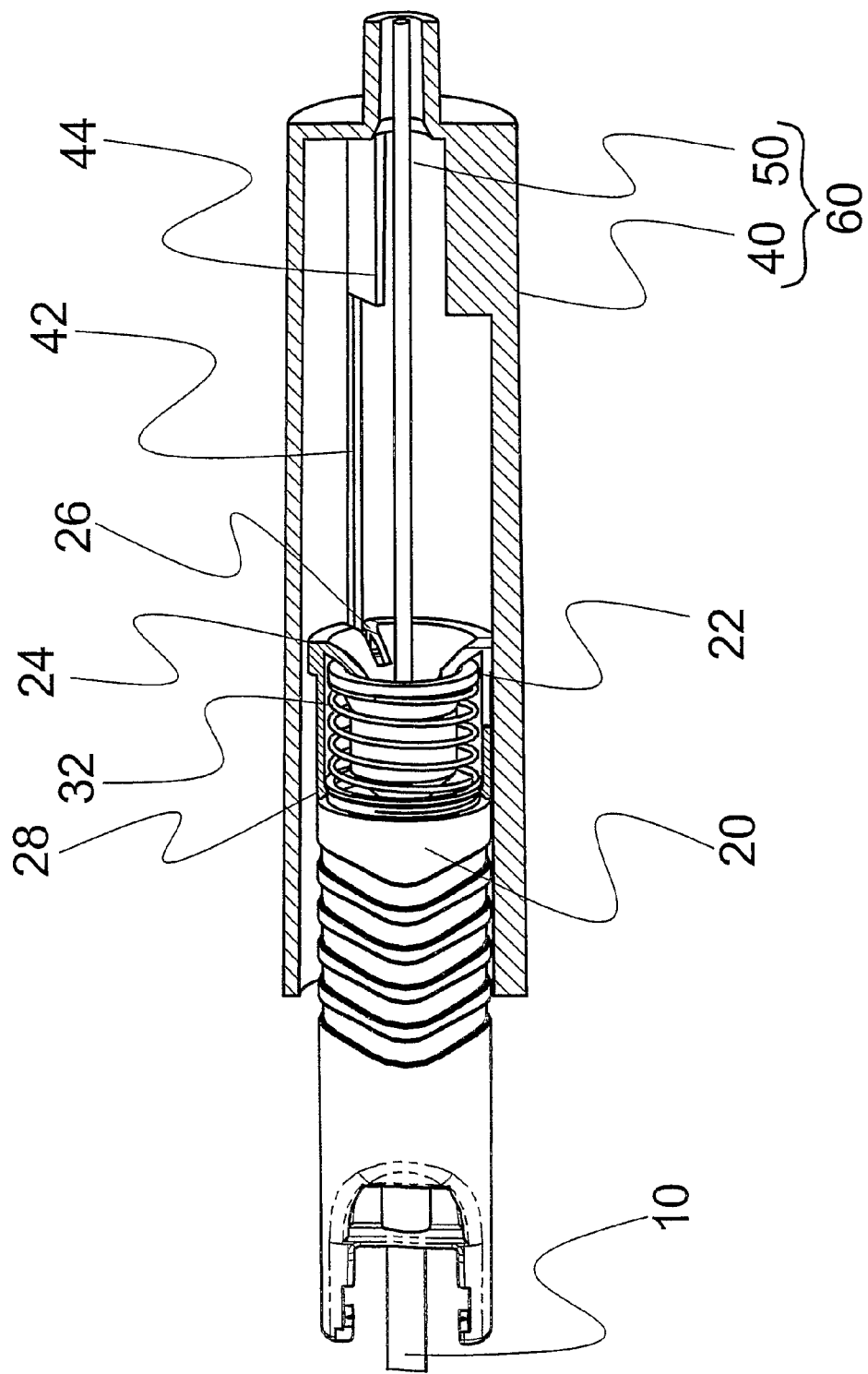
FIG. 3 is a perspective view of the embodiment of the safety housing shown in FIG. 1 and a cross-sectional view of the embodiment of the obturator handle shown in FIG. 1. The safety housing is shown with a recess on the aligning feature of the obturator handle.
Figure 4:
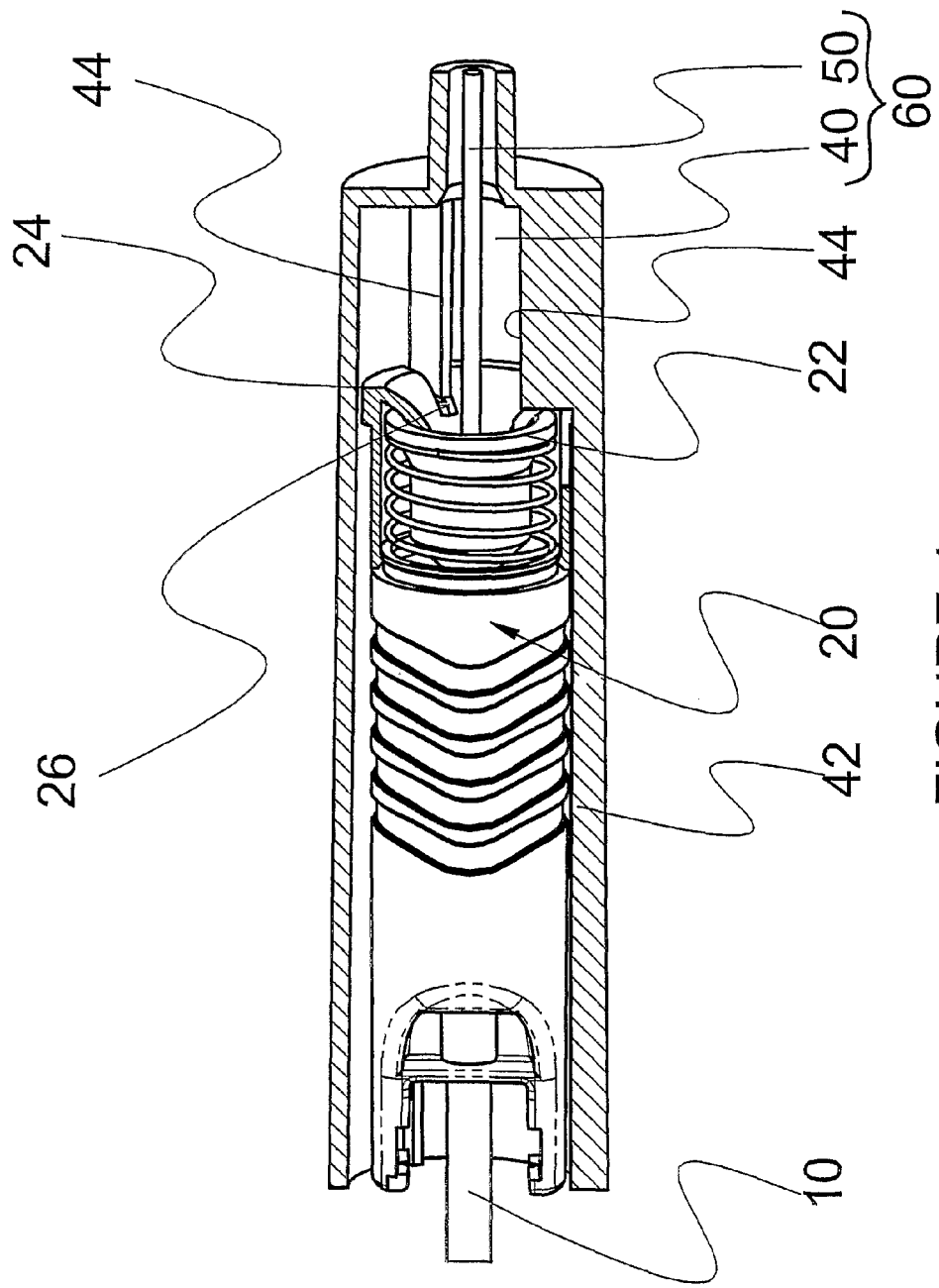
FIG. 4 is a perspective view of the embodiment of the safety housing shown in FIG. 1 and a cross-sectional view of the embodiment of the obturator handle shown in FIG. 1. The safety housing is shown with a reset geometry as initially contacted by a reset feature of the obturator via the recess of the safety housing.
Figure 5:
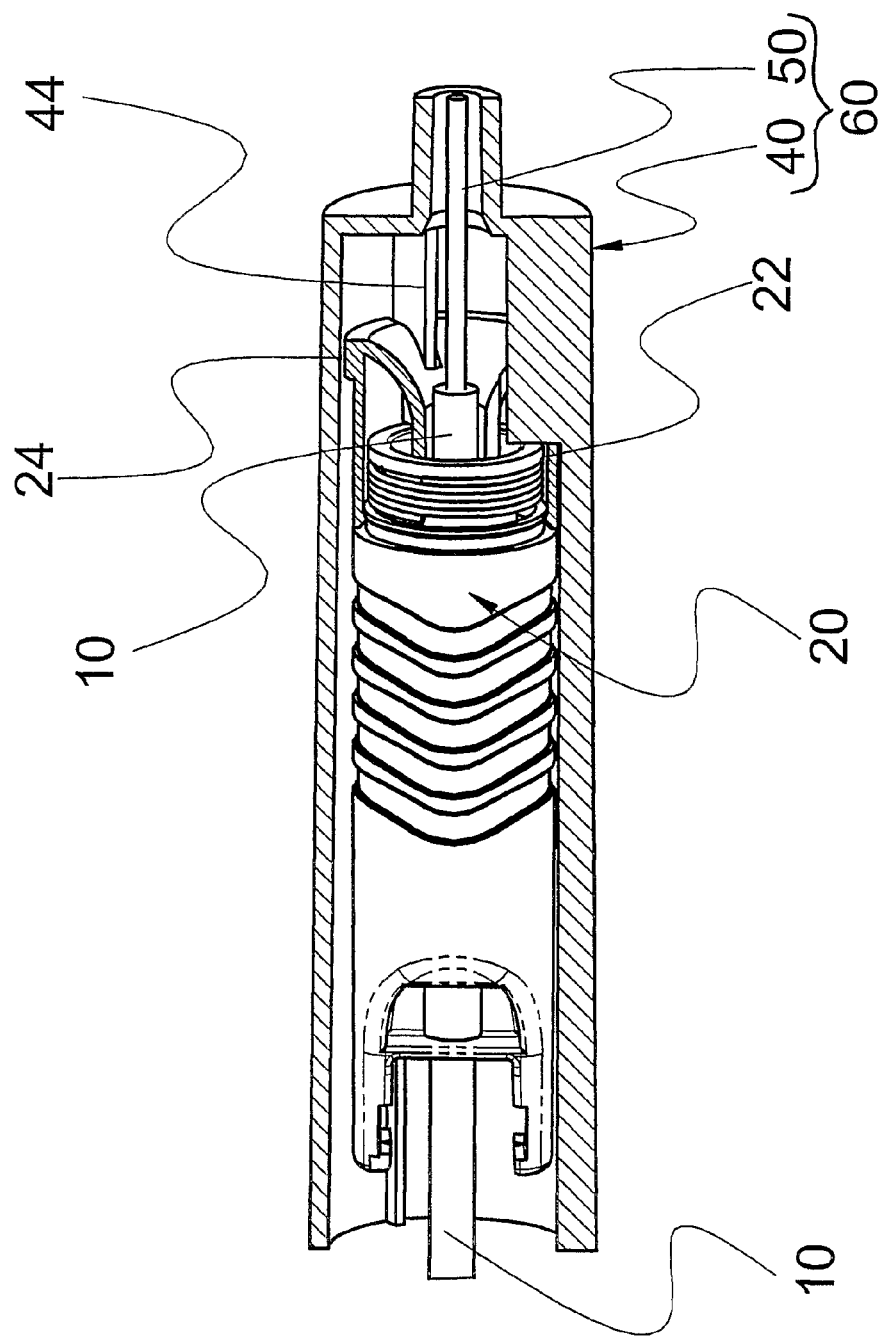
FIG. 5 is a perspective view of the embodiment of the safety housing shown in FIG. 1 and a cross-sectional view of the embodiment of the obturator handle shown in FIG. 1. The safety housing is shown with a reset geometry which has been moved to reset the safety housing by the reset feature of the obturator via the recess of the safety housing.

As indicated above, it is envisioned that it may be desirable to orient safety housing 20 for several medical procedures (e.g. resetting, activation, interfacing with other medical components, etc.). After medical needle 10 has been used in a medical procedure, safety housing 20 is locked onto medical needle 10, as shown in FIG. 1. Safety housing 20 cannot be subsequently moved unless it is mated with a reset device which acts as a key to unlock the binding member on the medical needle and reset the locked safety housing 20. Handle 40 is an example of a reset device which is configured to mate with safety housing 20 to reset safety housing 20. Handle 40 also has another function when used in another step of the medical procedure. FIGS. 3-5 depict handle 40 with an obturator 50 extending from a hub in handle 40. Handle 40 and obturator 50 together comprises an obturator device 60. Obturator 50 may be used to push tissue from a stylet such as tissue obtained in a bone biopsy.

Figure 2:
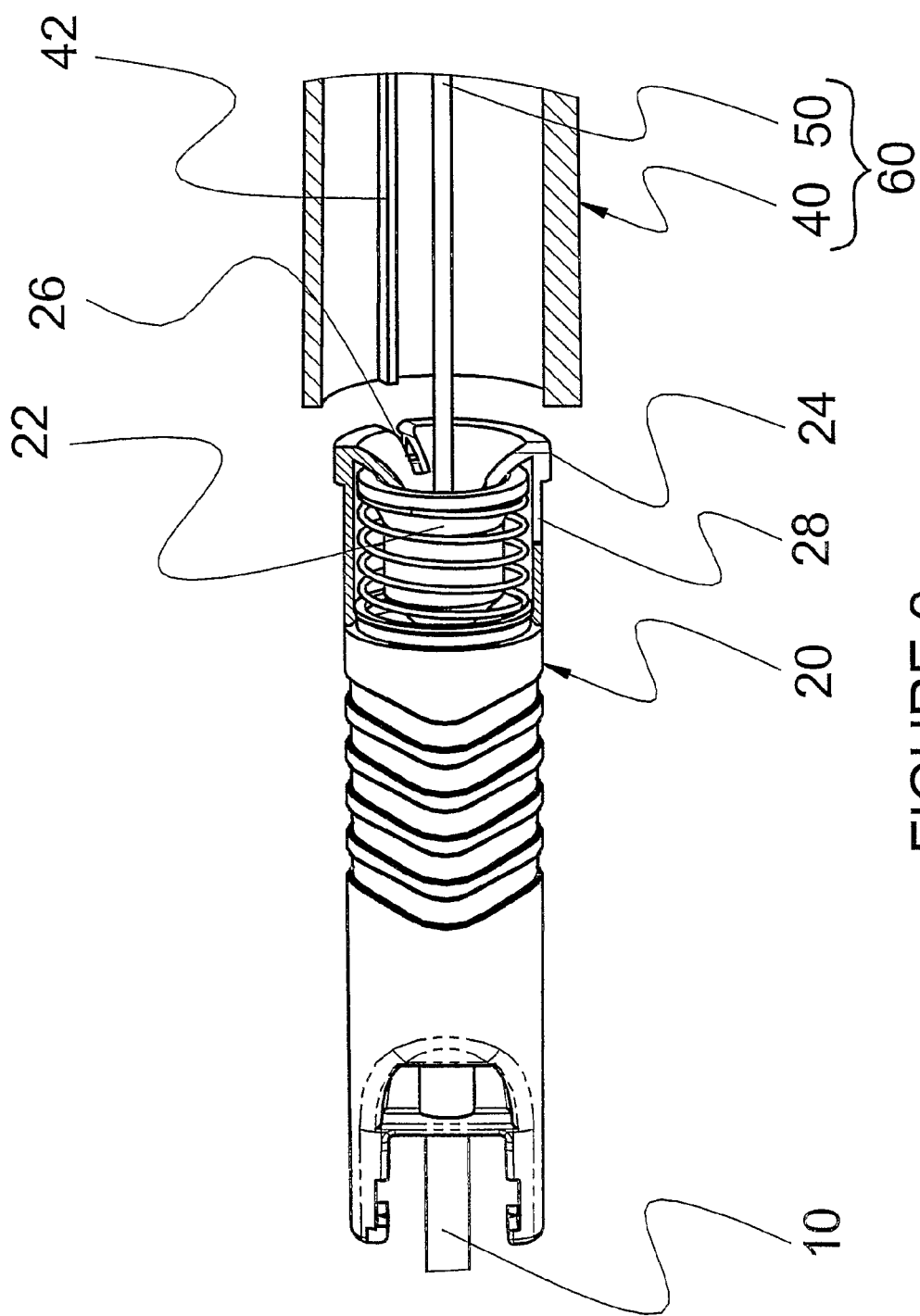
FIG. 2 is a perspective view of the embodiment of the safety housing shown in FIG. 1 and a cross-sectional view of the embodiment of the obturator handle shown in FIG. 1.

FIG. 2 shows a reset geometry 22 within safety housing 20 which is configured to de-activate a binding member (not shown) locked on medical needle 10. Reset geometry is defined as any component which is configured to de-activate a binding member. Reset geometry 22 is spring biased by spring 32 within safety housing 20 against raised rim 24.

Raised rim 24 has a plurality of slots 26 which provide limited access to reset geometry 22. Slots 26 are examples of access features which mate with aligning features such as ribs 42 of obturator handle 40. These ribs 42 and other aligning features may be integral to handle 40, or have any configuration that is intended to orient the safety housing 20 within handle 40. For example, ribs 42 extend radially inward and integrally from a wall of handle 40. As described in more detail with reference to FIGS. 3-5, it is desirable to align the safety housing 20 with ribs 42, on handle 40 to enable the reset geometry 22 of safety housing 20 and the reset features of handle 40 to be guided together to interact and reset the safety housing 20 on medical needle 10.

FIG. 3 shows safety housing 20 advancing within handle 40. Slots 26 and ribs 42 are mated such that reset geometry 22 rides on ribs 42 towards fins 44. Fins 44 provide an example of reset features. Fins 44 are inherently aligned with ribs 42 as fins 44 are integral extensions of ribs 42. Fins 44 also extend integrally inward from a wall of handle 40. Ribs 42 enable slots 26 to be aligned with fins 44 before reaching fins 44 which allows for a quick re-set of safety housing 20. Note that while the reset features are shown as part of the inner surface of a handle, the reset features may be located on an external surface or elsewhere such as an attachment to the safety housing.

Rim 24 is raised away from the body 28 of safety housing 20 which provides for enough clearance for safety housing 20 to easily move within handle 40. This embodiment shows the ribs 42 extending throughout handle 40. It is envisioned that the aligning features such as ribs 42 may start and end as required for the purpose of the medical procedure. In this embodiment it is desirable that the ribs extend throughout handle 40 so that the user may visually and tactilely align the safety housing 20 to handle 40. This also allows the safety housing 20 to be aligned for resetting while the user has full grip of both the safety housing 20 and handle 40.

Ribs 42 enable slots 26 to be aligned with fins 44 before reaching fins 44 which allows for a quick re-set of safety housing 20. As indicated above, slots 26 and ribs 42 are mated such that reset geometry 22 rides on ribs 42 towards fins 44. Fins 44 provide an example of reset features. Fins 44 are inherently aligned with ribs 42 as fins 44 are integral extensions of ribs 42.

In this embodiment the user does not have to look through two components to align them. Because the user would align externally, no pad printed marks or labels is required, no handle to housing orientation is required, and the user simply looks to align them like a screwdriver to a screw.

FIG. 4 shows fins 44 entering slots 26 and abutting recess geometry 22. In the embodiment depicted in FIGS. 1-5, there are three slots and a corresponding number of ribs and fins. Of course, other configurations and numbers of access features, alignment features and reset features utilized to achieve the functions disclosed herein are within the scope of the present invention.

FIG. 5 depicts spring 32 compressed by reset geometry 22 after fins 44 have been driven against reset geometry 22 via slots 26 of raised rim 24. Movement of reset geometry 22 proximally within safety housing 20 causes the binding member (not shown) to be unlocked on medical needle 10. Safety housing 20- and handle 40 can then be separated. After separation, safety housing can be slid away from the tip of the medical needle so that medical needle 10 can be re-used.

Figure 6:
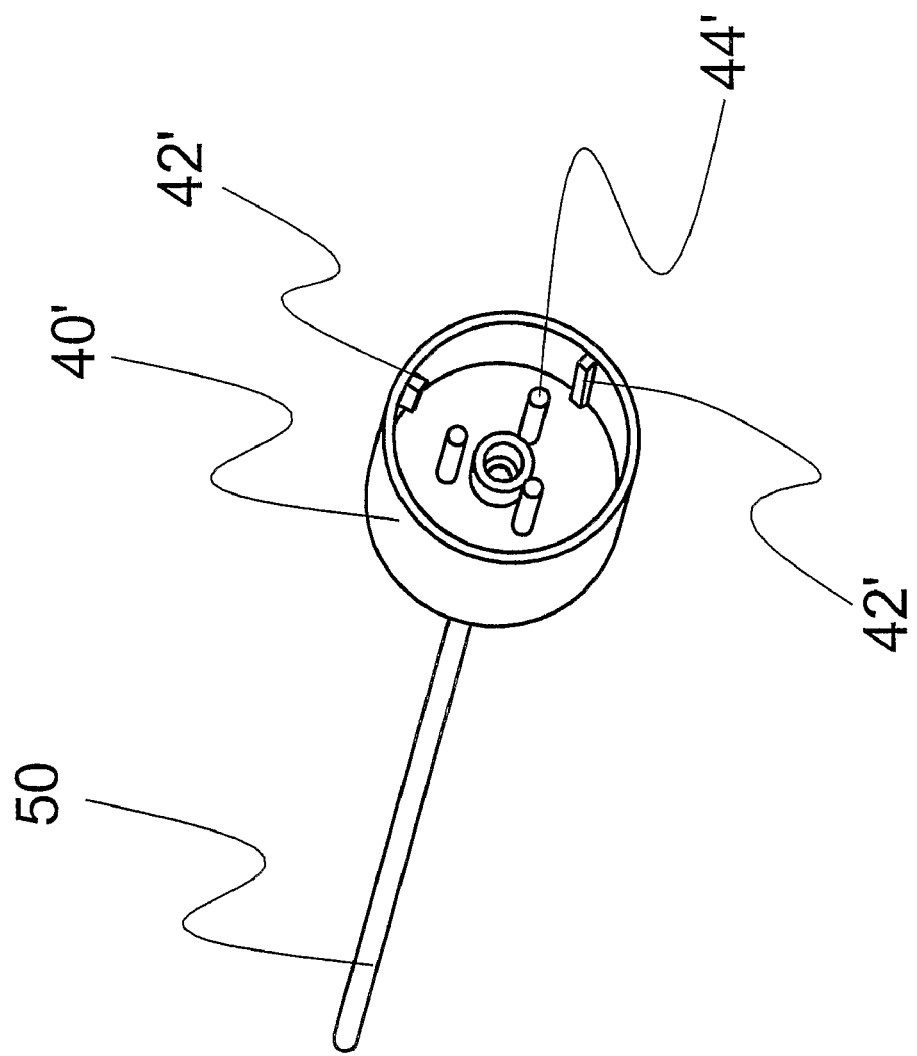
FIG. 6 is another embodiment of a reset device which can also be used as an obturator.

FIG. 6 depicts another embodiment of an obturator device 60' comprising an obturator 50 extending from a handle 40'. Handle 40' has a plurality of ribs 42' and reset prongs 44'. In contrast to the embodiment depicted in FIGS. 1-5, the alignment features and the reset features are not integral. In both embodiments, the reset devices has reset features which are configured to extend through the access features and be driven against the reset geometry to the move the reset geometry on the medical needle so that the safety housing no longer sheathes a tip of the medical needle. Note that obturator 50' is shown extending in the opposite direction as prongs 44'. In other embodiments, the reset features and the obturator extend in the same direction. In embodiments wherein the obturator and the safety features extend in the same direction, the obturator may be sized to fit within the medical needle.

The above description fully discloses the invention including preferred embodiments thereof. Without further elaboration, it is believed that one skilled in the art can use the preceding description to utilize the invention to its fullest extent. Therefore the examples and embodiments disclosed herein are to be construed as merely illustrative and not a limitation of the scope of the present invention in any way.

It will be apparent to those having skill in the art that changes may be made to the details of the above-described embodiments without departing from the essential characteristics and underlying principles of the invention. Embodiments of the invention in which an exclusive property or privilege is claimed are defined as follows.

The invention claimed is:

1. A medical needle system comprising:
    a medical needle shield apparatus comprising:
        a medical needle having a tip,
        a safety housing on the medical needle which is moveable to sheath the tip of the medical needle and can be reset more than one time to expose and re-expose the tip, and
        a reset geometry within the safety housing which is configured to be selectively driven to move the safety housing so that the tip of the medical needle is re-exposed after the safety housing sheathes the tip,
            wherein the safety housing has access features which provide access to the reset geometry via the safety housing; and
    a reset device comprising alignment features and reset features,
        wherein the alignment features mate with the access features to enable the safety housing to be aligned with respect to the reset features as the safety housing is advanced toward the reset features, and
        wherein the reset features are configured to extend through the access features and be driven against the reset geometry to move the reset geometry on the medical needle so that the safety housing no longer sheathes the tip of the medical needle.

2. The apparatus of claim 1, wherein the safety housing has a rim which has a greater diameter than a body of the safety housing so that the body of the safety housing does not contact the reset device.

3. The apparatus of claim 1, wherein the reset geometry is spring biased within the safety housing against a rim.

4. The apparatus of claim 1, wherein the access features are slots in a rim of the safety housing.

5. The apparatus of claim 1, wherein each reset feature extends radially inward further than each alignment feature extends radially inward.

6. The apparatus of claim 1, wherein each reset feature is a fin extending radially inward from a wall of the reset device.

7. The apparatus of claim 1, wherein each reset feature is an integral extension of one of the alignment features.

8. The apparatus of claim 1, wherein each reset feature is distinct from each alignment feature.

9. The apparatus of claim 1, wherein each alignment feature is a rib extending radially inward from a wall of the reset device.

10. The apparatus of claim 1, wherein the reset device is sized and shaped to receive the safety housing.

11. The apparatus of claim 1, wherein the reset device can also be used in a step of a medical procedure other than resetting the safety housing on the medical needle.

12. The apparatus of claim 1, wherein the medical needle is configured for bone biopsy.

13. A medical needle system comprising:
    a medical needle shield apparatus comprising:
        a medical needle having a tip,
        a safety housing on the medical needle which is moveable to sheath the tip of the medical needle and can be reset to expose the tip, and
        a reset geometry within the safety housing which is configured to be selectively driven to move the safety housing so that the tip of the medical needle is re-exposed after the safety housing sheathes the tip following a first injection,
            wherein the safety housing has access features which provide access to the reset geometry via the safety housing; and
    a reset device comprising alignment features and reset features,
        wherein the alignment features mate with the access features to enable the safety housing to be aligned with respect to the reset features as the safety housing is advanced toward the reset features, and
        wherein the reset features are configured to extend through the access features and be driven against the reset geometry to move the reset geometry on the medical needle so that the safety housing no longer sheathes the tip of the medical needle.

14. The apparatus of claim 13, wherein the reset geometry is spring biased within the safety housing against a rim.

15. The apparatus of claim 13, wherein each reset feature extends radially inward further than each alignment feature extends radially inward.

16. The apparatus of claim 13, wherein each reset feature is a fin extending radially inward from a wall of the reset device.

17. The apparatus of claim 13, wherein each reset feature is an integral extension of one of the alignment features.

18. The apparatus of claim 13, wherein each reset feature is distinct from each alignment feature.

19. An assembled medical needle system comprising:
    a medical needle shield apparatus comprising:
        a medical needle having a tip,
        a safety housing on the medical needle which is moveable to sheath the tip of the medical needle and can be reset to expose the tip following a first injection, and
        a reset geometry within the safety housing which is configured to be selectively driven to move the safety housing so that the tip of the medical needle is re-exposed after the safety housing sheathes the tip,
            wherein the safety housing has access features which provide access to the reset geometry via the safety housing; and
    a reset device comprising alignment features and reset features,
        wherein the alignment features mate with the access features to enable the safety housing to be aligned with respect to the reset features as the safety housing is advanced toward the reset features, and
        wherein the reset features are configured to extend through the access features and be driven against the reset geometry to move the reset geometry on the medical needle so that the safety housing no longer sheathes the tip of the medical needle.

20. The apparatus of claim 19, wherein each reset feature is distinct from each alignment feature.

* * * * *